US012646599B2

(12) United States Patent
Marcjan et al.

(10) Patent No.: US 12,646,599 B2
(45) Date of Patent: Jun. 2, 2026

(54) SYSTEMS AND METHODS FOR ANALYZING HEALTH DATA

(71) Applicant: Truveta, Inc., Bellevue, WA (US)

(72) Inventors: Cezary Antoni Marcjan, Redmond, WA (US); Chung Kei Wilson Lau, Seattle, WA (US); Ying Wei, Gilbert, IA (US)

(73) Assignee: Truveta, Inc., Bellevue, WA (US)

( * ) Notice: Subject to any disclaimer, the term of this patent is extended or adjusted under 35 U.S.C. 154(b) by 19 days.

(21) Appl. No.: 18/674,294

(22) Filed: May 24, 2024

(65) Prior Publication Data

US 2024/0412830 A1 Dec. 12, 2024

Related U.S. Application Data

(60) Provisional application No. 63/507,016, filed on Jun. 8, 2023.

(51) Int. Cl.
*G06F 17/00* (2019.01)
*G16H 10/60* (2018.01)

(52) U.S. Cl.
CPC .................................... *G16H 10/60* (2018.01)

(58) Field of Classification Search
CPC ...................................................... G16H 10/60
See application file for complete search history.

(56) References Cited

U.S. PATENT DOCUMENTS

| | | | |
|---|---|---|---|
| 7,428,494 B2 | 9/2008 | Hasan et al. | |
| 7,827,234 B2 * | 11/2010 | Eisenberger | ........... G16H 70/00 |
| | | | 709/203 |
| 9,710,431 B2 * | 7/2017 | Riskin | .................. G06F 40/279 |
| 10,534,816 B2 | 1/2020 | Gilder et al. | |

(Continued)

FOREIGN PATENT DOCUMENTS

| | | |
|---|---|---|
| CA | 2418239 C | 5/2014 |
| CN | 101194255 B | 6/2011 |

(Continued)

OTHER PUBLICATIONS

Bodenreider et al., Comparing the Representation of Anatomy in the FMA and SNOMED CT, AMIA 2006 Symposium Proceeding, pp. 46-50.

(Continued)

*Primary Examiner* — Greta L Robinson
(74) *Attorney, Agent, or Firm* — FORTEM IP LLP

(57) ABSTRACT

Systems and methods for efficient information retrieval for clinical data are provided. A document including one or more patient health records can be obtained and tokenized to generate a sequence of tokens, each corresponding to a word or sub-word within the document. A plurality of segments each containing a token sequence comprising a sub-set of the tokens are then generated. Next, a transformer model is used to process each of the plurality of segments to generate a corresponding word-level encoding for each segment. The word-level encodings for each of the segments are combined and fused to obtain document-level contextual data. The combined and fused word-level encodings can then be analyzed, such as to identify named entities and relationships between them.

20 Claims, 10 Drawing Sheets

(56) References Cited

U.S. PATENT DOCUMENTS

| | | | |
|---|---|---|---|
| 10,657,613 | B2 | 5/2020 | Bucur et al. |
| 11,151,125 | B1 | 10/2021 | Dwivedi et al. |
| 12,057,208 | B1 | 8/2024 | Esman |
| 12,086,287 | B2 | 9/2024 | Jensen et al. |
| 2008/0306872 | A1 | 12/2008 | Felsher |
| 2009/0030290 | A1 | 1/2009 | Kozuch et al. |
| 2010/0077006 | A1 | 3/2010 | El et al. |
| 2012/0046969 | A1 | 2/2012 | Schoenberg |
| 2014/0257045 | A1 | 9/2014 | Hu et al. |
| 2014/0330578 | A1 | 11/2014 | Pincus |
| 2016/0147945 | A1 | 5/2016 | Maccarthy et al. |
| 2016/0154978 | A1* | 6/2016 | Baker ................... G06F 16/285 |
| | | | 726/26 |
| 2016/0210427 | A1 | 7/2016 | Mynhier et al. |
| 2017/0103232 | A1* | 4/2017 | Scaiano ................. G16H 10/60 |
| 2017/0161439 | A1 | 6/2017 | Raduchel et al. |
| 2018/0089382 | A1 | 3/2018 | Allen et al. |
| 2018/0158552 | A1 | 6/2018 | Liu et al. |
| 2018/0322946 | A1 | 11/2018 | Ika et al. |
| 2019/0034590 | A1 | 1/2019 | Oren et al. |
| 2019/0034591 | A1 | 1/2019 | Mossin et al. |
| 2019/0057774 | A1 | 2/2019 | Velez et al. |
| 2019/0095478 | A1 | 3/2019 | Tankersley et al. |
| 2019/0371475 | A1 | 12/2019 | Oliveira et al. |
| 2020/0176098 | A1 | 6/2020 | Lucas et al. |
| 2020/0276098 | A1 | 9/2020 | Nabi et al. |
| 2022/0129584 | A1 | 4/2022 | Blackport et al. |
| 2022/0171747 | A1 | 6/2022 | Rajyaguru et al. |
| 2022/0222374 | A1 | 7/2022 | Antoniou et al. |
| 2023/0144503 | A1 | 5/2023 | Powers et al. |
| 2023/0147366 | A1 | 5/2023 | Marcjan et al. |
| 2023/0148326 | A1 | 5/2023 | Papel et al. |
| 2023/0162825 | A1 | 5/2023 | Nanduri et al. |
| 2024/0087687 | A1 | 3/2024 | Marcjan et al. |
| 2024/0370404 | A1 | 11/2024 | Burugapalli et al. |
| 2025/0232063 | A1 | 7/2025 | Shinn et al. |

FOREIGN PATENT DOCUMENTS

| | | |
|---|---|---|
| EP | 1994484 B1 | 3/2015 |
| WO | 2007084502 A1 | 7/2007 |
| WO | 2023081909 A1 | 5/2023 |
| WO | 2023081912 A1 | 5/2023 |
| WO | 2023081919 A1 | 5/2023 |
| WO | 2023081921 A1 | 5/2023 |

OTHER PUBLICATIONS

Devlin, Jacob et al., BERT: Pre-training of Deep Bidirectional Transformers for Language Understanding, Proceedings of NAACL-HLT 2019, pp. 4171-4186.

Jimenez-Ruiz et al., Logic-based assessment of the compatibility of UMLS ontology sources, Journal of Biomedical Semantics, 2011, 2(Suppl 1): S2.

Luong et al., Multi-Task Sequence to Sequence Learning, published as a conference paper at ICLR, 2016, 10 pages.

Xue, Linting et al., ByT5: Towards a Token-Free Future with Pre-trained Byte-to-Byte Models, endeavarXiv:2105.13626v3 [cs. CL] Mar. 8, 2022, 16 pages.

Xue, Linting et al., mT5: A Massively Multilingual Pre-trained Text-to-Text Transformer, arXiv:2010.11934v3 [cs.CL] Mar. 11, 2021, 17 pages.

Ahmad, Arab , et al., "MDMP: A new algorithm to create inverted index files in BigData, using MapReduce", 2017 7th International Conference on Computer and Knowledge Engineering (ICCKE), IEEE, Oct. 26, 2017 (Oct. 26, 2017), pp. 372-378.

Garfinkel, Simson L., "De-identification of personal information NIST IR 8053", NIST, National Institute of Standards and Technology (NIST) Oct. 21, 2015 (Oct. 21, 2015), pp. 1-54, XP061056032, DOI: 10.6028/NIST.IR.8053.

Sweeney, Latanya , "k-anonymity: a model for protecting privacy k-Anonymity: A Model for Protecting Privacy 1", International Journal on Uncertainty, Oct. 31, 2002 (Oct. 31, 2002), pp. 557-570, XP055268614, Retrieved from the Internet: URL:https://epic.org/ privacy/reidentificat ion/Sweeney Article.pdf [retrieved on Apr. 26, 2016] the whole document.

Taneja, Himanshu , et al., "Preserving Privacy of Patients Based on Re-identification Risk", Procedia Computer Science, Elsevier, Amsterdam, NL, vol. 70, Nov. 21, 2015 (Nov. 21, 2015), pp. 448-454, XP029309606, ISSN: 187.7-0509, DOI: 10.1016/J.PROCS.2015. 10.073 the whole document.

Uwe, Roth , "A Generalized View on Pseudonyms and Domain Specific Local Identifiers. Lessons Learned from Various Use Cases", The International Journal on Advances in Security, vol. 7, No. 3-4, Dec. 31, 2014 (Dec. 31, 2014), pp. 76-92, XP093019165, ISSN: 1942-2636 the whole document.

* cited by examiner

200

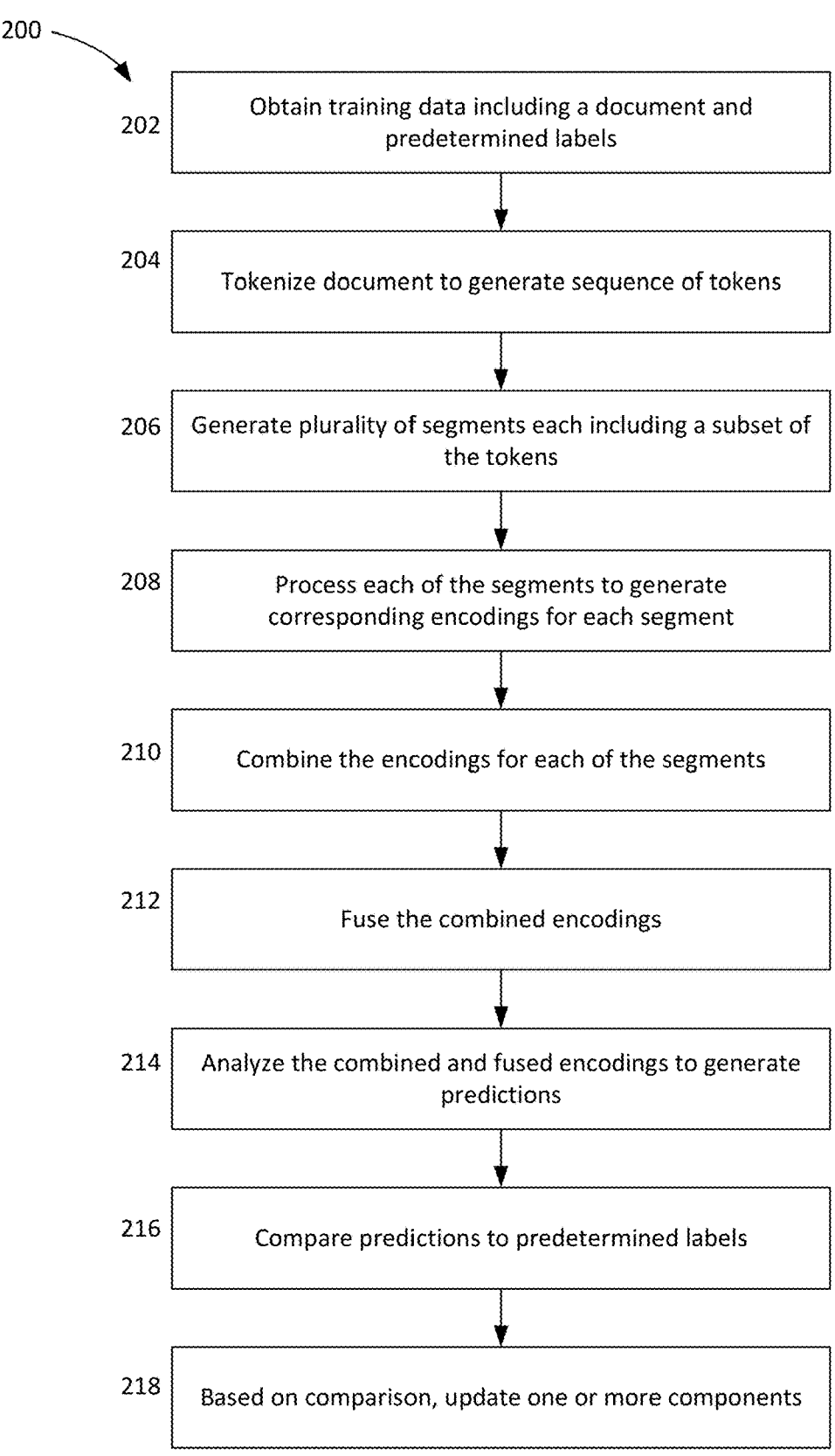

202     Obtain training data including a document and predetermined labels

204     Tokenize document to generate sequence of tokens

206     Generate plurality of segments each including a subset of the tokens

208     Process each of the segments to generate corresponding encodings for each segment 210     Combine the encodings for each of the segments 212     Fuse the combined encodings 214     Analyze the combined and fused encodings to generate predictions 216     Compare predictions to predetermined labels 218     Based on comparison, update one or more components

| 602 | Obtain document |
| 204 | Tokenize document to generate sequence of tokens |
| 206 | Generate plurality of segments each including a subset of the tokens |
| 208 | Process each of the segments to generate corresponding encodings for each segment |
| 210 | Combine the encodings for each of the segments |
| 212 | Fuse the combined encodings |
| 214 | Analyze the combined and fused encodings |

SYSTEMS AND METHODS FOR ANALYZING HEALTH DATA

CROSS-REFERENCE TO RELATED APPLICATIONS

This application claims the benefit of priority to U.S. Patent Application No. 63/507,016, filed Jun. 8, 2023, which is herein incorporated by reference in its entirety.

The following applications are herein incorporated by reference in their entireties: U.S. patent application Ser. No. 18/053,504, titled "Health Data Platform and Associated Methods," filed Nov. 8, 2022; U.S. patent application Ser. No. 18/053,540, titled "Systems and Methods for Indexing and Searching Health Data," filed Nov. 8, 2022; U.S. patent application Ser. No. 18/053,643, titled "Systems and Methods for De-Identifying Patient Data," filed Nov. 8, 2022; and U.S. patent application Ser. No. 18/053,654, titled "Systems and Methods for Data Normalization," filed Nov. 8, 2022.

TECHNICAL FIELD

The present technology generally relates to healthcare, and in particular, to systems and methods for information retrieval from unstructured text such as health data records.

BACKGROUND

Healthcare entities, such as hospitals, clinics, and laboratories, collect, store and process patient data for payment processing, analytics, and fostering research. While aggregated patient data presents a promising opportunity for researchers and clinicians, searching and analyzing this aggregated data presents several challenges. Recent developments in machine learning hold promise for analyzing and retrieving data. However, many approaches are limited in the length of input text that can be evaluated. Accordingly, there remains a need for improved systems and methods for analyzing health data.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIG. 2 illustrates an example routine for training an information retrieval system in accordance with embodiments of the present technology.

DETAILED DESCRIPTION

Figure 1A:
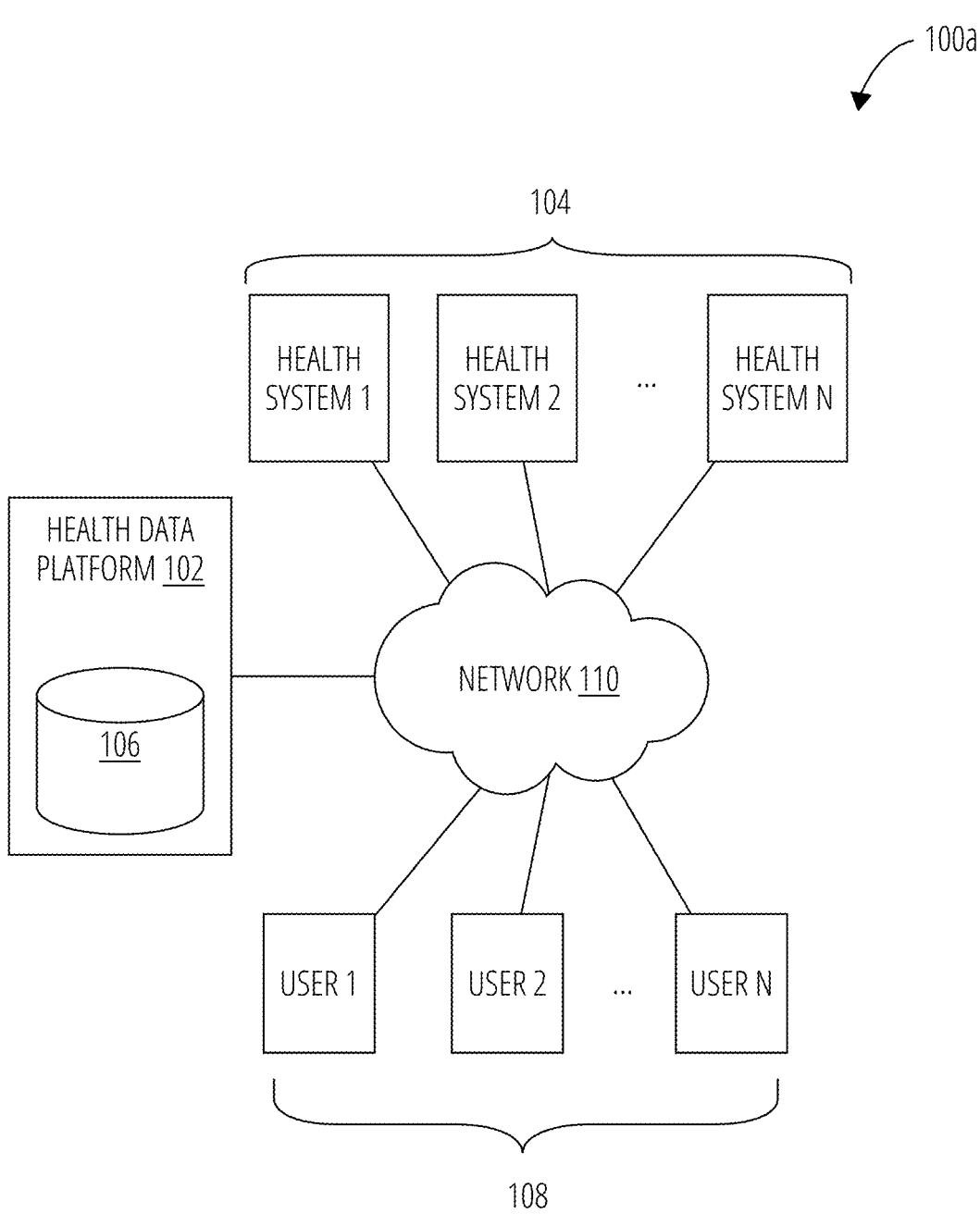
FIG. 1A is a schematic diagram of a computing environment in which a health data platform can operate, in accordance with embodiments of the present technology.

The present technology relates to systems and methods for retrieving and evaluating health data. Health data is often stored in a variety of different formats and supplied by a variety of different entities, such as hospitals, insurance carriers, universities, research institutions, and others. In various embodiments, health data can be aggregated from multiple different sources and converted into a standard format such that search and analysis across the aggregated data is possible. Optionally, the patient data can be de-identified and/or otherwise partially or fully anonymized before being aggregated. In some embodiments, the disclosed techniques provide a network-based patient data management method that acquires and aggregates patient information from various sources into a uniform or common format, stores the aggregated patient information, and notifies health care providers and/or patients, such as after information is updated via one or more communication channels, when new results to a periodic search are available, and so on. In some cases, the acquired patient information may be provided by one or more users through an interface, such as a graphical user interface, that provides remote access to users over a network so that any one or more of the users can provide at least one updated patient record in real time, such as a patient record in a format other than the uniform or common format, including formats that are dependent on a hardware and/or software platform used by a user providing the patient information.

In some instances, aggregated health data can be quite large, for example including hundreds of thousands, millions, or tens of millions of patient records. The health data may be represented by a timeline of events for each patient or patient record, with each event representing an action or change in the patient's medical history (e.g., being diagnosed with a certain condition, having a particular medication administered, etc.).

Researchers and clinicians may wish to query and analyze aggregated health data to identify correlations, trends, causal factors associated with particular outcomes, or any other such relationships. In some examples, a researcher may wish to identify the set of patients that match particular constraints. Those constraints may include temporal aspects (e.g., relative and absolute times of particular events on the patient's timeline), event property values, relationships between events, etc. For example, a query may be intended to find all male patients who were (i) diagnosed with condition C in the last 10 years, (ii) were given medication M within 4 weeks of the diagnosis, and (iii) recorded a lab measurement of type L and score S within 1 year of the diagnosis.

To evaluate these aspects, a given document corpus (e.g., a patient's medical records) must be analyzed to identify certain entities (e.g., instances of medication M, lab measurement of type L, etc.) and/or relationships between entities (e.g., a dosage D of medication M). Machine learning techniques involving language models have shown promise in named entity recognition (NER) and relational extraction (RE) tasks. These tasks benefit from document-level contextual information, which provides richer context features to deep learning models, enabling them to make more accurate and consistent predictions on the input text. Existing document-level systems utilize pre-trained language models to encode contextual features using GPUs for efficient training. However, such systems are limited in their ability to process long documents due to the constraints of language models and GPU memory. In particular, the maximum input window for a given language model is often insufficient for an entire document (e.g., a single clinical note in a patient's medical history). While it is possible to divide a document into samples and separately evaluate each sample, this approach can lead to poorer analysis, as relations between one entity in one sample and another entity in a different sample may be missed.

In various embodiments, the present technology solves these and other problems by providing efficient information retrieval systems and methods that are capable of processing long documents. According to some implementations, a given document can be divided into segments so as to overcome the maximum sequence length limitation of a given language model. For instance, a document can be tokenized to generate a sequence of tokens, which can then be grouped into segments. Each segment can include a subset of the tokens such that the total length for each segment is less than the input window length for a given language model. Each segment can then be processed via the language model to generate word-level encodings. Optionally, the language model first generates sub-word-level encodings, which are then used to obtain word-level encodings.

Next, the word-level encodings corresponding to each of the segments can be combined (e.g., concatenated) and fused (e.g., using a Bi-Long Short-Term Memory (Bi-LSTM) operator) to generate document-level contextual data. This data allows each word encoding to incorporate information from the document-level context. This combined and fused data can then be analyzed (e.g., to predict or identify named entities, relations between entities, or other features).

In some implementations, longer documents can be split into samples for training of an information retrieval system. This can be useful to overcome the limitations associated with limited memory available to GPUs (which are typically used for language model computations). As one example, a document can be divided into a plurality of segments as described previously. The segments can then be grouped together sequentially into samples. Each sample may then be processed independently for training, with no interaction during training and optimization between samples from the same document. However, within each sample, the encoding can be concatenated and fused together in order for the model to learn the document level context.

According to another aspect of the present technology, a hybrid inferencing model can be used to more efficiently perform inferencing tasks on larger documents. In particular, the larger document can be tokenized and divided into segments as noted above. This step can be performed using a CPU. The segments can then be fed through a language model, which may run on a GPU, to provide encodings. However, rather than combine and fuse these encodings on the same GPU that ran the language model, the combine and fuse steps can be performed instead on a CPU. The analysis of the combined and fused encodings can likewise be performed via a CPU. By performing the intensive attention computation of the language model on the GPU, while performing the remainder of the operations on the CPU, this approach can take advantage of the much larger memory available to the CPU than the GPU. As a result, much larger documents can be evaluated using this hybrid inferencing approach to identify entities and extract relations between them without having to divide the document into samples.

Although many examples described herein relate to health data, and to patient records in particular, embodiments of the present technology can be applied to retrieving, evaluating, and/or analyzing any suitable data type.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The headings provided herein are for convenience only and do not interpret the scope or meaning of the claimed present technology. Embodiments under any one heading may be used in conjunction with embodiments under any other heading.

I. HEALTH DATA PLATFORM

Figure 1B:
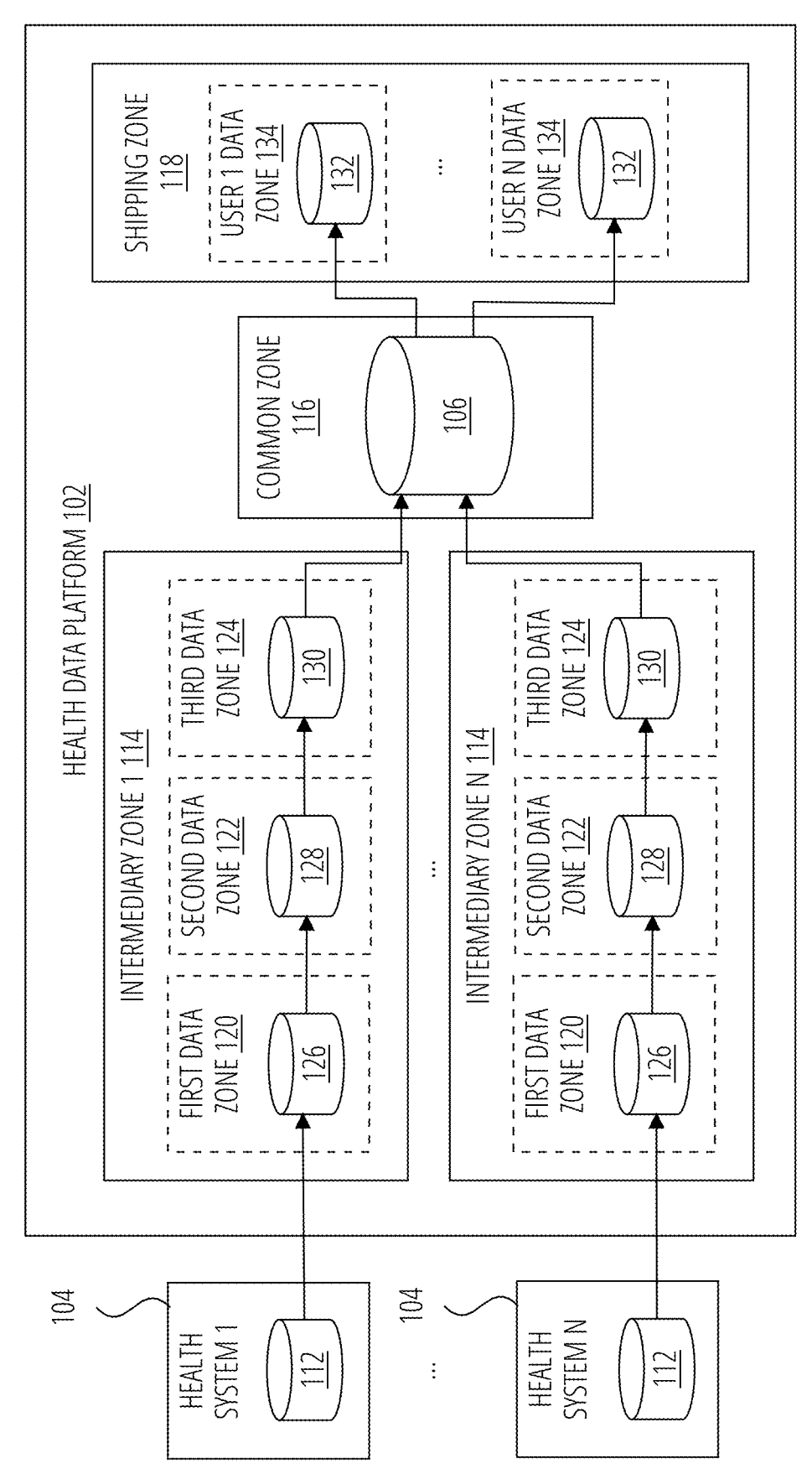
FIG. 1B is a schematic diagram of a data architecture that can be implemented by a health data platform, in accordance with embodiments of the present technology.
Figure 1C:
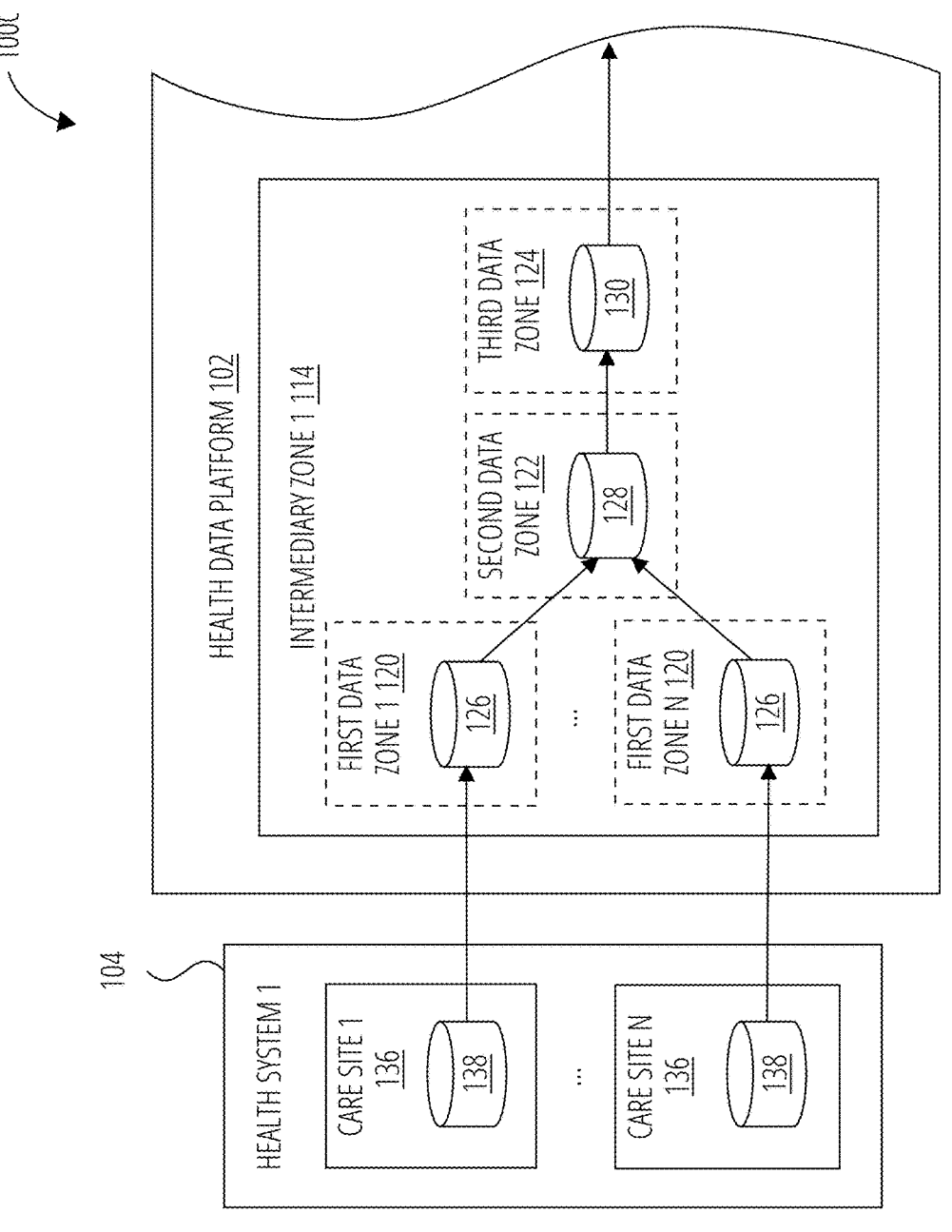
FIG. 1C is a schematic diagram of a data architecture that can be implemented by a health data platform, in accordance with embodiments of the present technology.

FIGS. 1A and 1B provide a general overview of a health data platform configured in accordance with embodiments of the present technology. Specifically, FIG. 1A is a schematic diagram of a computing environment 100a in which a health data platform 102 can operate, and FIG. 1B is a schematic diagram of a data architecture 100b that can be implemented by the health data platform 102.

Referring first to FIG. 1A, the health data platform 102 is configured to receive health data from a plurality of health systems 104, aggregate the health data into a common data repository 106, and allow one or more users 108 to access the health data stored in the common data repository 106. As described in further detail below, the common data repository 106 can store health data from multiple different health systems 104 and/or other data sources in a uniform schema, thus allowing for rapid and convenient searching, analytics, modeling, and/or other applications that would benefit from access to large volumes of health data.

The health data platform 102 can be implemented by one or more computing systems or devices having software and hardware components (e.g., processors, memory) configured to perform the various operations described herein. For example, the health data platform 102 can be implemented as a distributed "cloud" server across any suitable combination of hardware and/or virtual computing resources. The health data platform 102 can communicate with the health system 104 and/or the users 108 via a network 110. The network 110 can be or include one or more communications networks, such as any of the following: a wired network, a wireless network, a metropolitan area network (MAN), a local area network (LAN), a wide area network (WAN), a virtual local area network (VLAN), an internet, an extranet, an intranet, and/or any other suitable type of network or combinations thereof.

The health data platform 102 can be configured to receive and process many different types of health data, such as patient data. Examples of patient data include, but are not limited to, the following: age, gender, height, weight, demographics, symptoms (e.g., types and dates of symptoms), diagnoses (e.g., types of diseases or conditions, date of diagnosis), medications (e.g., type, formulation, prescribed dose, actual dose taken, timing, dispensation records), treatment history (e.g., types and dates of treatment procedures, the healthcare facility or provider that administered the treatment), vitals (e.g., body temperature, pulse rate, respiration rate, blood pressure), laboratory measurements (e.g., complete blood count, metabolic panel, lipid panel, thyroid panel, disease biomarker levels), test results (e.g., biopsy results, microbiology culture results), genetic data, diagnostic imaging data (e.g., X-ray, ultrasound, MRI, CT), clinical notes and/or observations, other medical history (e.g., immunization records, death records), insurance information, personal information (e.g., name, date of birth, social security number (SSN), address), familial medical history, and/or any other suitable data relevant to a patient's health. In some embodiments, the patient data is provided in the form of electronic health record (EHR) data, such as structured EHR data (e.g., schematized tables representing orders, results, problem lists, procedures, observations, vitals, microbiology, death records, pharmacy dispensation records, lab values, medications, allergies, etc.) and/or unstructured EHR data (e.g., patient records including clinical notes, pathology reports, imaging reports, etc.). A set of patient data relating to the health of an individual patient may be referred to herein as a "patient record."

The health data platform 102 can receive and process patient data for an extremely large number of patients, such as thousands, tens of thousands, hundreds of thousands, millions, tens of millions, or hundreds of millions of patients. The patient data can be received continuously, at predetermined intervals (e.g., hourly, daily, weekly, monthly), when updated patient data is available and/or pushed to the health data platform 102, in response to requests sent by the health data platform 102, or suitable combinations thereof. Thus, due to the volume and complexity of the patient data involved, many of the operations performed by the health data platform 102 are impractical or impossible for manual implementation.

Optionally, the health data platform 102 can also receive and process other types of health data. For example, the health data can also include facility and provider information (e.g., names and locations of healthcare facilities and/or providers), performance metrics for facilities and providers (e.g., bed utilization, complication rates, mortality rates, patient satisfaction), hospital formularies, health insurance claims data (e.g., 835 claims, 837 claims), supply chain data (e.g., information regarding suppliers of medical devices and/or medications), device data (e.g., device settings, indications for use, manufacturer information, safety data), health information exchanges and patient registries (e.g., immunization registries, disease registries), research data, regulatory data, and/or any other suitable data relevant to healthcare. The additional health data can be received continuously, at predetermined intervals (e.g., hourly, daily, weekly, monthly), as updated data is available, upon request by the health data platform 102, or suitable combinations thereof.

The health data platform 102 can receive patient data and/or other health data from one or more health systems 104. Each health system 104 can be an organization, entity, institution, etc., that provides healthcare services to patients. A health system 104 can optionally be composed of a plurality of smaller administrative units (e.g., hospitals, clinics, labs, or groupings thereof), also referred to herein as "care sites." The health data platform 102 can receive data from any suitable number of health systems 104, such as one, two, four, five, ten, fifteen, twenty, thirty, forty, fifty, hundreds, or thousands or more different health systems 104. Each health system 104 can include or otherwise be associated with at least one computing system or device (e.g., a server) that communicates with the health data platform 102 to transmit health data thereto. For example, each health system 104 can generate patient data for patients receiving services from the respective health system 104, and can transmit the patient data to the health data platform 102. As another example, each health system 104 can generate operational data relating to the performance metrics of the care sites within the respective health system 104, and can transmit the operational data to the health data platform 102.

Optionally, the health data platform 102 can receive health data from other data sources besides the health systems 104. For example, the health data platform 102 can receive health data from one or more databases, such as public or licensed databases on drugs, diseases, medical ontologies, demographics and/or other patient data, etc. (e.g., SNOMED CT, RxNorm, ICD-10, FHIR, LOINC, UMLS, OMOP, LexisNexis, state vaccine registries). In some embodiments, this additional health data provides metadata that is used to process, analyze, and/or enhance patient data received from the health systems 104, as described below.

The health data platform 102 can perform various data processing operations on the received health data, such as de-identifying health data that includes patient identifiers, converting the health data from a health system-specific format into a uniform format, and/or enhancing the health data with additional data. Subsequently, the health data platform 102 can aggregate the processed health data in the common data repository 106. The common data repository 106 can be or include one or more databases configured to store health data from multiple health systems 104 and/or other data sources. The health data in the common data repository 106 can be in a uniform schema or format to facilitate downstream applications. For example, the health data platform 102 performs additional data processing operations on the health data in the common data repository 106, such as analyzing the health data (e.g., using machine learning models and/or other techniques), indexing or otherwise preparing the health data for search and/or other applications, updating the health data as additional data is received, and/or preparing the health data for access by third parties (e.g., by performing further de-identification processes). Additional details of some of the operations that can be performed by the health data platform 102 are described below with respect to FIG. 1B.

The health data platform 102 can allow one or more users 108 (e.g., researchers, healthcare professionals, health system administrators) to access the aggregated health data stored in the common data repository 106. Each user 108 can communicate with the health data platform 102 via a computing device (e.g., personal computer, laptop, mobile device, tablet computer) and the network 110. For example, a user 108 can send a request to the health data platform 102 to retrieve a desired data set, such as data for a population of patients meeting one or more conditions (e.g., diagnosed with a particular disease, receiving particular medication, belonging to a particular demographic group). The health data platform 102 can search the common data repository 106 to identify a subset of the stored health data that fulfills the requested conditions, and can provide the identified subset to the user 108. Optionally, the health data platform 102 can perform additional operations on the identified subset of health data before providing the data to the user, such as de-identification and/or other processes to ensure data security and patient privacy protection.

FIG. 1B illustrates the data architecture 100*b* of the health data platform 102, in accordance with embodiments of the present technology. The health data platform 102 can be subdivided into a plurality of discrete data handling zones, also referred to herein as "zones" or "domains." Each zone is configured to perform specified data processing operations and store the data resulting from such operations. For example, in the illustrated embodiment, the health data platform 102 includes a plurality of intermediary zones 114 (also known as "embassies") that receive and process health data from the health systems 104, a common zone 116 that aggregates the data from the intermediary zones 114 in the common data repository 106, and a shipping zone 118 that provides selected data for user access. Each zone can include access controls, security policies, privacy rules, and/or other measures that define data isolation boundaries tailored to the sensitivity level of the data contained within that zone. The flow of data between zones can also be strictly controlled to mitigate the risk of privacy breaches and/or other data security risks.

In the illustrated embodiment, each of the health systems 104 includes at least one health system database 112. The health system database 112 can store health data produced by the respective health system 104, such as patient data for the patients receiving healthcare services from the health system 104, operational data for the health system 104, etc. The patient data stored in the health system database 112 can include or be associated with identifiers such as the patient's name, address (e.g., street address, city, county, zip code), relevant dates (e.g., date of birth, date of death, admission date, discharge date), phone number, fax number, email address, SSN, medical record number, health insurance beneficiary number, account number, certificate or license number, vehicle identifiers and/or serial numbers (e.g., license plate numbers), device identifiers and/or serial numbers, web URL, IP address, finger and/or voice prints, photographic images, and/or any other characteristic or information that could uniquely identify the patient. Accordingly, the patient data can be considered to be PHI (e.g., electronic PHI (ePHI)), which may be subject to strict regulations on disclosure and use.

As shown in FIG. 1B, health data can be transmitted from the health systems 104 to the health data platform 102 via respective secure channels and/or over a communications network (e.g., the network 110 of FIG. 1A). The health data can be transmitted continuously, at predetermined intervals, in response to pull requests from the health data platform 102, when the health systems 104 push data to the health data platform 102, or suitable combinations thereof. For example, some or all of the health systems 104 can provide a daily feed of data to the health data platform 102.

The health data from the health systems 104 can be received by the intermediary zones 114 of the health data platform 102. In some embodiments, the intermediary zones 114 are configured to process the health data from the health systems 104 to prepare the data for aggregation in the common zone 116. For example, each intermediary zone 114 can de-identify the received health data to remove or otherwise obfuscate identifying information so that the health data is no longer classified as PHI and can therefore be aggregated and used in a wide variety of downstream applications (e.g., search, analysis, modeling). The intermediary zone 114 can also normalize the received health data by converting the data from a health system-specific format to a uniform format suitable for aggregation with health data from other health systems 104. As shown in FIG. 1B, each intermediary zone 114 can receive health data from a single respective health system 104. The intermediary zones 114 can be isolated from each other such that health data across different health systems 104 cannot be combined with each other or accessed by unauthorized entities (e.g., a health system 104 other than the health system 104 that originated the data) before patient identifiers have been removed.

In the illustrated embodiment, each intermediary zone 114 includes a plurality of data zones that sequentially process the health data from the respective health system 104. For example, in the illustrated embodiment, each intermediary zone 114 includes a first data zone 120 (also known as a "landing zone"), a second data zone 122 (also known as an "enhanced PHI zone"), and a third data zone 124 (also known as an "enhanced DeID zone").

As shown in FIG. 1B, the health data from each health system 104 can initially be received and processed by the first data zone 120 (landing zone). The first data zone 120 can implement one or more data ingestion processes to extract relevant data and/or filter out erroneous or irrelevant data. The data ingestion processes can be customized based on the particular health system 104, such as based on the data types and/or formats produced by the health system 104. Accordingly, the first data zones 120 within different intermediary zones 114 can implement different data ingestion processes, depending on the particular data output of the corresponding health system 104. The data resulting from the data ingestion processes can be stored in a first database 126 within the first data zone 120. The data can remain in the first database 126 indefinitely or for a limited period of time (e.g., no more than 30 days, no more than 1 year, etc.), e.g., based on the preferences of the respective health system 104, security considerations, and/or other factors. The data in the first database 126 can still be considered PHI because the patient identifiers have not yet been removed from the data. Accordingly, the first data zone 120 can be subject to relatively stringent access controls and data security measures.

The data produced by the first data zone 120 can be transferred to the second data zone 122 (enhanced PHI zone). In some embodiments, the data received from the first data zone 120 is initially in a non-uniform format, such as a format specific to the health system 104 that provided the data. Accordingly, the second data zone 122 can implement one or more data normalization processes to convert the data into a unified, normalized format or schema (e.g., a standardized data model). Optionally, data normalization can include enhancing, enriching, annotating, or otherwise supplementing the health data with additional data (e.g., health metadata received from databases and/or other data sources). The data resulting from these processes can be stored in a second database 128 within the second data zone 122. The data can remain in the second database 128 indefinitely or for a limited period of time (e.g., no more than 30 days, 1 year, etc.), e.g., based on the preferences of the respective health system 104, security considerations, and/or other factors. The data stored in the second database 128 can still be considered PHI because the patient identifiers have not yet been removed from the data. Accordingly, the second data zone 122 can also be subject to relatively stringent access controls and data security measures, similar to the first data zone 120.

The data produced by the second data zone 122 can be transferred to the third data zone 124 (enhanced DeID zone). The third data zone 124 can implement one or more de-identification processes to remove and/or modify identifiers from the data so that the data is no longer classified as PHI. The de-identification processes can include, for example, modifying the data to remove, alter, coarsen, group, and/or shred patient identifiers, and/or removing or suppressing certain patient records altogether. For example, a patient record can be suppressed if the record would still potentially be identifiable even after the identifiers have been removed and/or modified (e.g., if the record shows a diagnosis of an extremely rare disease). In some embodiments, the de-identification processes also include producing tokens that allow data from the same patient to be tracked without using the original identifiers. The resulting de-identified data can be stored in a third database 130 within the third data zone 124. The data can remain in the third database 130 indefinitely or for a limited period of time (e.g., no more than 30 days, 1 year, etc.), e.g., based on the preferences of the respective health system 104, security considerations, and/or other factors. Because the data stored in the third database 130 is no longer considered PHI, the third data zone 124 can have less stringent access controls and data security measures than the first and second data zones 120, 122.

The de-identified data produced by each intermediary zone 114 can be transferred to a common zone 116 within the health data platform 102 via respective secure channels. The common zone 116 can include the common data repository 106 that stores aggregated health data from all of the health systems 104. As discussed above, the data stored in the common data repository 106 has been de-identified and/or normalized into a uniform schema, and can therefore be used in many different types of downstream applications. For example, the common zone 116 can implement processes that analyze the data in the common data repository 106 using machine learning and/or other techniques to produce various statistics, analytics (e.g., cohort analytics, time series analytics), models, knowledge graphs, etc. As another example, the common zone 116 can implement processes that index the data in the common data repository 106 to facilitate search operations.

The data stored in the common data repository 106 can be selectively transferred to the shipping zone 118 of the health data platform 102 for access by one or more users 108 (not shown in FIG. 1B). In the illustrated embodiment, the shipping zone 118 includes a plurality of user data zones 134. Each user data zone 134 can be customized for a particular user 108, and can store and expose a selected subset of data for access by that user 108. The user data zones 134 can be isolated from each other so that each user 108 can only access data within their assigned user data zone 134. The amount, type, and/or frequency of data transferred to each user data zone 134 can vary depending on the data requested by the user 108 and the risk profile of the user 108. For example, the user 108 can send a request to the health data platform 102 (e.g., via the network 110 of FIG. 1A) for access to certain data in the common data repository 106 (e.g., data for patients who have been diagnosed with a particular disease, belong to a particular population, have received a particular treatment procedure, etc.). The common zone 116 can implement a search process to identify a subset of the data in the common data repository 106 that fulfills the request parameters. Optionally, depending on the risk profile of the user 108, the common zone 116 can perform additional de-identification processes and/or apply other security measures to the identified data subset. The identified data subset can then be transferred to the user data zone 134 for access by the user 108 (e.g., via a secure channel in the network 110 of FIG. 1A). Additional details regarding indexing and search of data within the user data zones 134 are described below in Sections II and III.

The data architecture 100b illustrated in FIG. 1B can be configured in many different ways. For example, although the intermediary zones 114 are illustrated in FIG. 1B as having three data zones, in other embodiments, some or all of the intermediary zones 114 can include fewer or more data zones. Any of the zones illustrated in FIG. 1B can alternatively be combined with each other into a single zone, or can be subdivided into multiple zones. Any of the processes described herein as being implemented by a particular zone can instead be implemented by a different zone, or can be omitted altogether.

II. EXAMPLE SYSTEMS AND METHODS FOR EFFICIENT INFORMATION RETRIEVAL

Document-level information extraction is an important task in natural language processing, particularly in domains such as healthcare, in which long and complex documents are prevalent. However, existing approaches typically process documents sentence by sentence using a pipeline of Named Entity Recognition (NER) and Relation Extraction (RE). These sentence-level approaches have limitations such as using limited context features for prediction, difficulty in extracting long-distance relations, and low efficiency. On the other hand, document-level contextual information provides richer context features to deep learning models, enabling them to make more precise predictions on the input text.

Although it is possible to use pre-trained language models to encode contextual features at a document-level, such approaches are limited in processing long documents due to language model and GPU memory constraints. One existing approach is to split a long document into fixed-length segments and process each segment separately to meet the constraints of language models and GPUs. This approach limits the language models to only encode information within a segment, leading to incomplete contextual information. Another approach is to design specific language models via specially designed attention mechanisms, which enables longer document processing but still suffers from a maximum sequence length limit.

Another challenge in fine-tuning language models is the limited on-board memory of GPUs. Fine-tuning language models usually consumes a relatively large amount of GPU memory, making it difficult to accommodate long documents. Current approaches typically split a document into several samples according to the maximum memory of a single GPU and process the samples separately. However, splitting a document can lead to insufficient context information for information extraction. The context information could be enriched if longer documents could be processed in a single process. Thus, addressing the constraints of GPU memory is beneficial for fine-tuning language models with long documents.

The present technology improves upon prior approaches by providing an effective and efficient information extraction system to address existing limitations and to enable the processing of long documents. In various examples, a long document can be encoded by dividing into segments and then fusing the segments at both the segment-level and GPU level, thus overcoming the constraints of both the language model and the GPU.

A. Model Training for Clinical Information Analysis and Retrieval

As noted previously, existing approaches to encoding long documents suffer several drawbacks. Embodiments of the present technology provide an information retrieval system for clinical data that is capable of handling document-level information retrieval tasks, even with long input texts.

FIG. 2 illustrates an example routine 200 for training an information retrieval system. The routine 200 can begin in block 202 with obtaining training data including one or more documents (e.g., clinical notes) and corresponding predetermined data labels. The labels may be, for instance, named entities, relations between entities, or other suitable data labels. In the context of health care data, entities might include, for instance, particular medications, procedures, symptoms, tests, test results, dates, or times, identified individuals or roles, etc. Relations between entities might include, for instance, administered-in-the-amount-of (linking a dosage to a particular drug), time-of-condition (linking a particular diagnosis or symptom with a date or time), or any other suitable relationship between entities identified in the training data.

The routine 200 continues in block 204 with tokenizing the document to generate a sequence of tokens. Tokenization in the context of machine learning and natural language processing refers to the process of breaking down a text document into smaller units, commonly referred to as "tokens." These tokens can be as small as individual words, or even smaller components, such as sub-words, syllables, or characters. In some implementations, the document can be preprocessed before tokenizing. This may include tasks such as converting all the text to lowercase, removing punctuation or special characters, or removing HTML tags (if the document is a web page), etc.

The simplest form of tokenization is word tokenization, in which a document is split on whitespace to produce a list of words. However, more complex forms of tokenization may be used. For example, sentence tokenization, where the document is split into sentences, or sub-word tokenization, where words are split into smaller meaningful components, can be used depending on the desired configuration and performance of the system.

In some implementations, after tokenization, additional postprocessing may be performed on the tokens. This may include stemming (reducing words to their root form), lemmatization (reducing words to their base or dictionary form), or removing stop words (commonly used words like "the", "a", "an", which may not carry much information for many tasks).

In various examples, any suitable tokenization algorithm may be used. For instance, for sub-word tokenization, byte-pair encoding (BPE), unigram language model tokenization, or morphological tokenization may be used. One example approach involves using Bidirectional Encoder Representations from Transformers (BERT) tokenization. BERT is a transformer-based model introduced by Google, which relies on a specific tokenization strategy known as Word-Piece tokenization. However, in various implementations, any suitable tokenization technique can be used.

At block 206, the routine 200 generates a plurality of segments each including a subset of the tokens. This operation effectively divides the input document into segments so as to overcome the maximum sequence length limitation of language models. In some embodiments, each segment can contain at most L sub-words after tokenization into word pieces, where L is the maximum sequence length that a selected language model can process. For instance, given a sequence of n tokens and a language model with a maximum sequence length of L, the tokens can be sequentially divided into k segments with each segment containing L tokens with $k = \lceil n/L \rceil$.

In some implementations, additional rules can be applied to avoid dividing a word into two segments. For instance, when a given word is tokenized into two or more sub-words, rules can be applied so that all the sub-words for that word are grouped into the same segment. This same approach can be extended to sentence level (or paragraph level, or otherwise), in which all tokens derived from a given sentence are grouped into the same segment.

The routine 200 continues in block 208 with processing each of the segments to generate corresponding word-level encodings for each segment. In this step, a selected language model M can be used to encode each segment r ($1 \leq r \leq k$) with $n_r$ tokens, resulting in a token-level encoding $S_r \in R^{(n_r \times d)}$, where d is the number of features from the language model M. In some examples, the language model can be transformer-based, and in particular examples can be the Bidirectional Encoder Representations from Transformers (BERT) model mentioned previously. However, in various implementations, any suitable transformer-based language model or other architecture can be used to generate encodings based on input tokens that have been grouped into segments.

If the tokens were generated at a sub-word level, and the language model M operates at the sub-word level, then the resulting token-level encoding can be converted into word-level encoding. In some examples, this can be achieved by using an index matrix. The index matrix $I_R$ for a segment r is an $m_r \times n_r$ matrix (where m is the number of words in the segment and n is the number of sub-words), where each row corresponds to a word and each column corresponds to a sub-word (e.g., a word piece). A non-zero entry (i, j) indicates that the sub-word j is part of word i, with a value of $1/c_i$, where word is split into $c_i$ sub-words. The word encoding is computed by $S'_r = I_r S_r$.

Next, in block 210, the routine 200 involves combining the encodings for each of the segments. For instance, word-level encodings can be concatenated or otherwise combined together. In one implementation, concatenation of the word-level encodings takes the form of $docE = [e_1; e_2; \ldots; e_k]$.

At block 212, the routine 200 fuses the combined word-level encodings to obtain document-level contextual data. In some implementations, to enhance information fusion across the various segments, a Bidirectional Long-Term Short Memory (Bi-LTSM) operator can be employed on the combined word-level encodings, which allows each word-level encoding to incorporate information from the document-level context: $S_{doc} = LSTM([S'_1; S'_2; \ldots; S'_k])$. The use of a Bi-LSTM operator is provided as one example among many suitable approaches for fusion of information across the various word-level encodings of the segments. Other approaches can utilize, for instance, a convolutional neural network (CNN), multi-head attention models, or other suitable algorithms.

The routine 200 continues in block 214 with analyzing the combined and fused word-level encodings to generate predictions. The predictions may include, for instance, one or more named entity recognition (NER) predictions and/or one or more relation extraction (RE) predictions.

In some examples, a BIO tagging scheme can be used to tag each word and obtain the tagging prediction of a word w by feeding its encoding into a Multi-Layer Perceptron (MLP). If $s_i$ denotes the encoding of the ith word, the prediction values $z_i \in R^{C_{NER}}$ can be computed by $z_i = W_2 \circ_1 (W_1 s_i + b_1) + b_2$, where $W_1$, $W_2$, $b_1$, and $b_2$ are trainable parameters, $\sigma_1$ is an element-wise activation function, and $C_{NER}$ is the number of entity classes. To capture the contextual dependencies between named entities and enhance the overall performance of the NER task, a conditional random fields (CRF) model can be applied on top of the prediction values, which outputs a final prediction label sequence $c = (c_1, C_2, \ldots, c_m)$ with the ith word assigned the entity type $c_i$, where $0 \leq c_i \leq C_{NER}$.

To predict relations, predictions can be generated for each pair of entities (which can be generated from the NER prediction results). In one example approach, to extract entities from NER predictions, words that are tagged as "B" are considered as entities, and their encodings are used as corresponding entities' feature representations. For each entity pair (h, t), the prediction can be based on both entities' feature representations ($s_h$, $s_t$), their entity types embedding ($q_h$, $q_t$), relative distance embedding ($u_{h,t}$), and average encoding of all words between them ($v_{h,t}$), which results in an overall encoding for this entity pair: $s_{h,t} = [s_h; s_t; q_t; u_{h,t}; v_{h,t}]$.

The prediction values $z_{h,t} \in R^{C_{RE}}$ can be computed by: $z_{h,t} = W_4 \circ_2 (W_3 s_{h,t} + b_3) + b_4$, where $W_3$, $W_4$, $b_3$, and $b_4$ are trainable parameters, $\sigma_2$ is an element-wise activation function, and $C_{RE}$ is the number of relation classes. The relation between entities (h, t) can be assigned the relation type $c_{h,t} = \arg \max_j z_{h,t}[j]$.

At block 216, the generated predictions are compared to the predetermined labels included as training data (block 202), and at block 218, based on the comparison, one or more components of the system can be updated. For example, the weights of one or more of: the language model M used to generate word-level encodings (block 208) or the algorithm used to fuse the combined word-level encodings (block 212) can be adjusted. Additionally or alternatively, other aspects of the system may be updated, such as the tokenization scheme, the analysis scheme (block 214), or any other suitable components.

In some implementations, the system can be optimized using different loss functions for different tasks. For example, cross-entropy loss and adaptive margin loss calculations can be used for NER and RE predictions, respectively. The adaptive margin loss is inspired by the hinge loss and enables the maximum distance from training examples to the decision boundary. To achieve this, a separation class can be introduced. If the logit of a class is higher than that of the separation class, it will be predicted as a positive relation class for the pair of entities. The maximum separation between negative and positive classes can be achieved via the separation class.

The routine 200 can be repeated iteratively over a corpus of training data to improve the performance of the system. In various implementations, some portions of the routine 200 can be performed on one or more central processor units (CPUs) while other portions of the routine 200 can be performed on one or more graphics processor units (GPUs). For instance, blocks 204 and 206 can be performed via CPU(s), while blocks 208-214 may be performed via GPUs. In alternative implementations, only block 208 (processing segments using a language model or other transformer to generate encodings) may be performed via GPU(s), while other tasks can be performed via CPU(s). As noted elsewhere herein, this approach can be useful when dealing with particularly large documents, as the CPU has access to much larger memory than the GPU.

Figure 3:
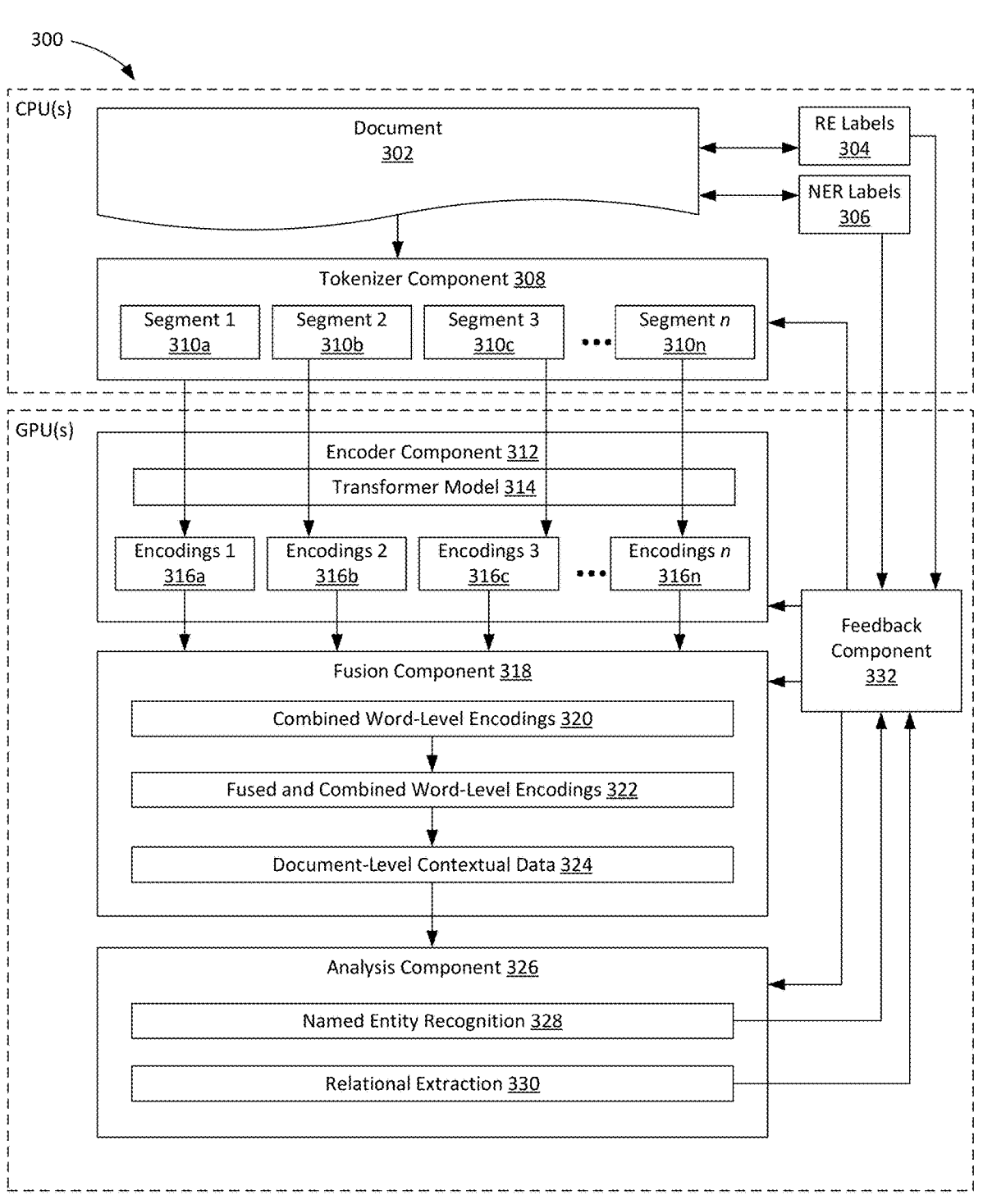
FIG. 3 is a schematic block diagram of training an information retrieval system in accordance with embodiments of the present technology.

FIG. 3 illustrates an example system 300 suitable for use in the routine 200 described above with respect to FIG. 2. As illustrated in FIG. 3, in the system 300, a document 302 can be provided with associated data labels including relational extraction (RE) labels 304 and named entity recognition (NER) labels. The document 302 can be provided to a tokenizer component 308. As described above, the document can be tokenized to generate a sequence of tokens (e.g., at the word or sub-word level) which can then be sequentially grouped together into segments 310*a-n* (collectively "segments 310").

Each of the segments 310 can then be provided to an encoder component 312, which includes a transformer model 314 (e.g., a language model or other suitable architecture) for generating corresponding encodings 316*a-n* (collectively "encodings 316") for each of the segments 310. In various examples, the length of each segment 310 can be less than a maximum input window for the transformer model 314 used to generate the encodings 316. In some implementations, the tokens can be generated at a sub-word level, and the transformer model 314 can first generate encodings at a sub-word level using those tokens. These sub-word-level encodings can be used to generate word-level encodings as desired (e.g., using an index matrix as noted previously).

Next, the encodings 316 are provided to a fusion component 318, which can first generate combined word-level encodings 320, for instance by concatenating the individual encodings 316*a-n*. These combined word-level encodings 320 can then be fused to generate fused and combined word-level encodings 322 and/or document-level contextual data 324. As noted previously, this fusion can take the form of a Bi-LSTM operator, a convolutional neural network, a multi-head attention model, or any other suitable algorithm that processes the combined word-level encodings 320 to provide document-level contextual data 324.

This document-level contextual data 324 (which may include fused and combined word-level encodings 322) is then provided to an analysis component 326, which includes an NER prediction component 328 and an RE prediction component 330. As described above, these predictions can be generated using the document-level contextual data. In some implementations, a BIO tagging scheme is utilized to identify entities, and heads and tails in relations between entities.

The predictions from analysis component 326 can be provided to a feedback component 332, which compares the predictions to the predetermined data labels accompanying the training data (e.g., RE labels 304 and NER labels 306). Based on this comparison, the system 300 can be optimized, for instance by varying weights of the tokenizer component 308, encoder component 312 (e.g., the transformer model 314), the fusion component 318, and/or by varying parameters of the analysis component 326.

Figure 4:
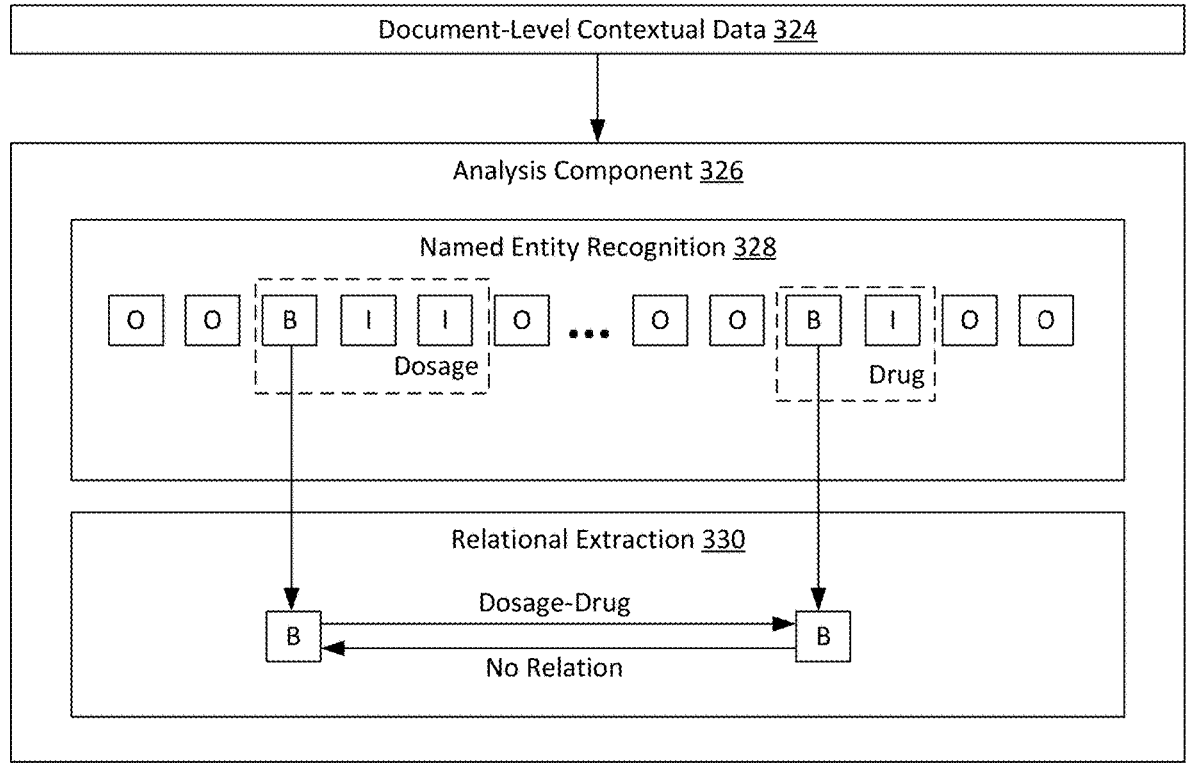
FIG. 4 is a schematic block diagram with details of an example analysis component of the informational retrieval system shown in FIG. 3.

FIG. 4 is a schematic block diagram with details of an example analysis component of the informational retrieval system shown in FIG. 3. As shown in FIG. 4, the document-level contextual data 324 (which may include the fused and combined word-level encodings 322) is provided to the analysis component 326. The NER prediction component 328 can utilize a BIO tagging scheme to tag each word and obtain the tagging prediction of a word w by feeding its encoding into a multi-layer perceptron. "B" tokens can be treated as entities for use in the relation extraction prediction component 330.

In the illustrated example, a first entity is identified as "dosage" and a second entity is identified as "drug." For the RE tasks, the word encoding of the head and tail entities, the word distance embedding between them, entity type embeddings for the head and tail entities, and context features can all be used to determine relations. In some examples, the context feature of a pair of entities is encoded by aggregating the word encodings between the two entities. The RE predictions can be obtained by concatenating these features and feeding them into another multi-layer perceptron for prediction. In the illustrated example, the RE predictions identify a "dosage-drug" relationship in a direction from the first entity ("dosage") and the second entity ("drug"), while not identifying any relationship in the opposite direction.

Figure 5:
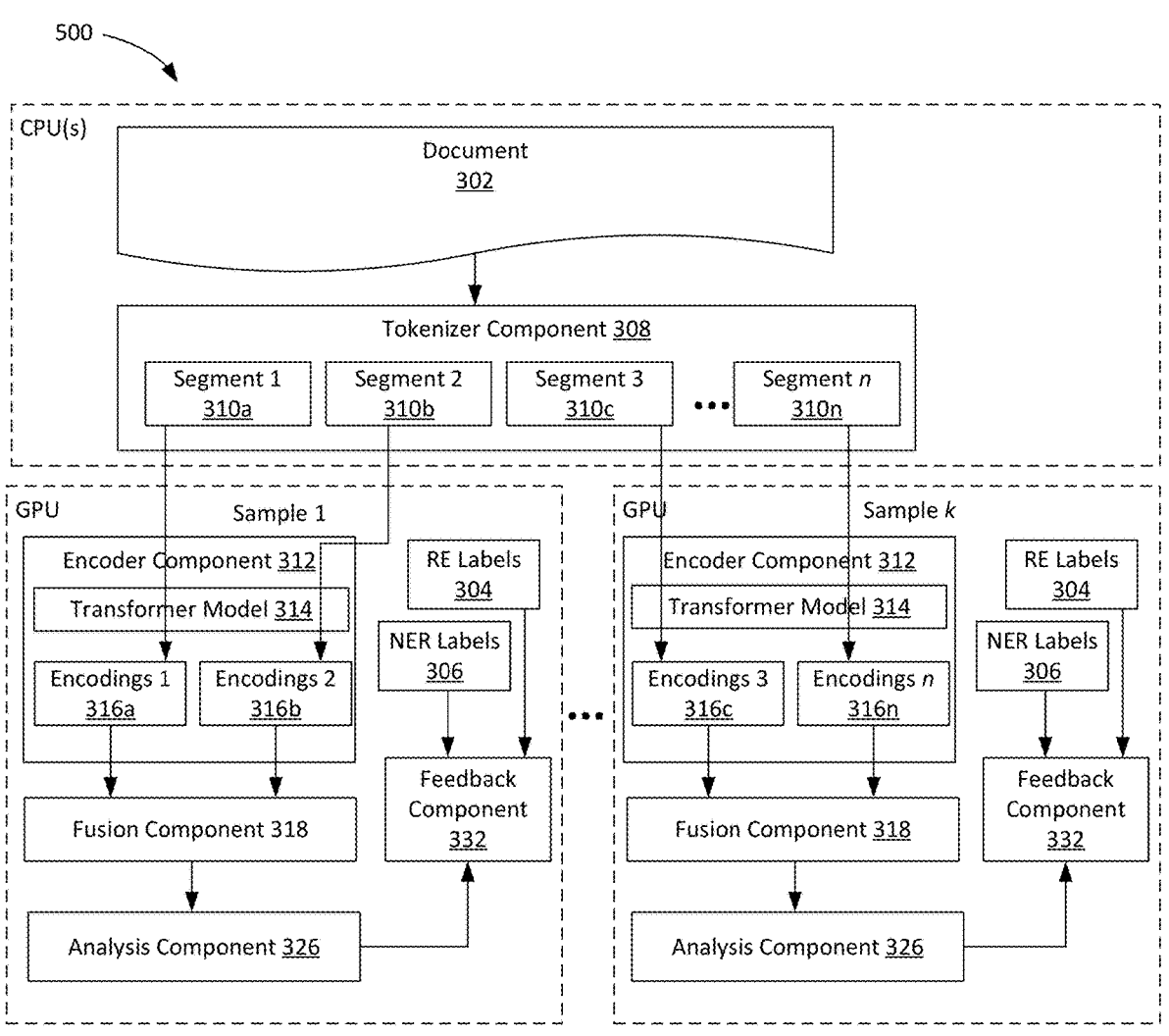
FIG. 5 is a schematic block diagram of training an information retrieval system with large document sizes in accordance with embodiments of the present technology.

FIG. 5 is a schematic block diagram of training an information retrieval system with large document sizes in accordance with embodiments of the present technology. While the approach described above with respect to FIGS. 2-4 allows the use of a transformer or other language model on large documents with token lengths that exceed the maximum input window for the transformer, the process may still be inefficient and slow due to constraints associated with the GPU used for the encoding process.

When fine-tuning language models, GPUs are often utilized to speed up the process. However, their memory capacity is limited, and it may not be sufficient to store the features of long documents in addition to the language model. This limitation restricts the maximum length of a document that can be processed. Specifically, if a single GPU can handle at most H segments, and each segment contains L tokens, the longest document that can be processed would be H×L tokens.

This limitation can be overcome utilizing the architecture shown in FIG. 5. As illustrated, after tokenizing the document 302 and generating a plurality of segments 310, the segments can be grouped into samples (e.g., sample 1 through sample k), which can be each be assigned to a different GPU for language model processing via encoding component 312. As shown in FIG. 5, each sample can be processed separately via a separate GPU, including predictions and optimization tasks. This approach enables the language models to process a document with a much larger number of tokens by distributing the workload across multiple different GPUs.

B. Inferencing for Clinical Information Analysis and Retrieval

Figure 6:
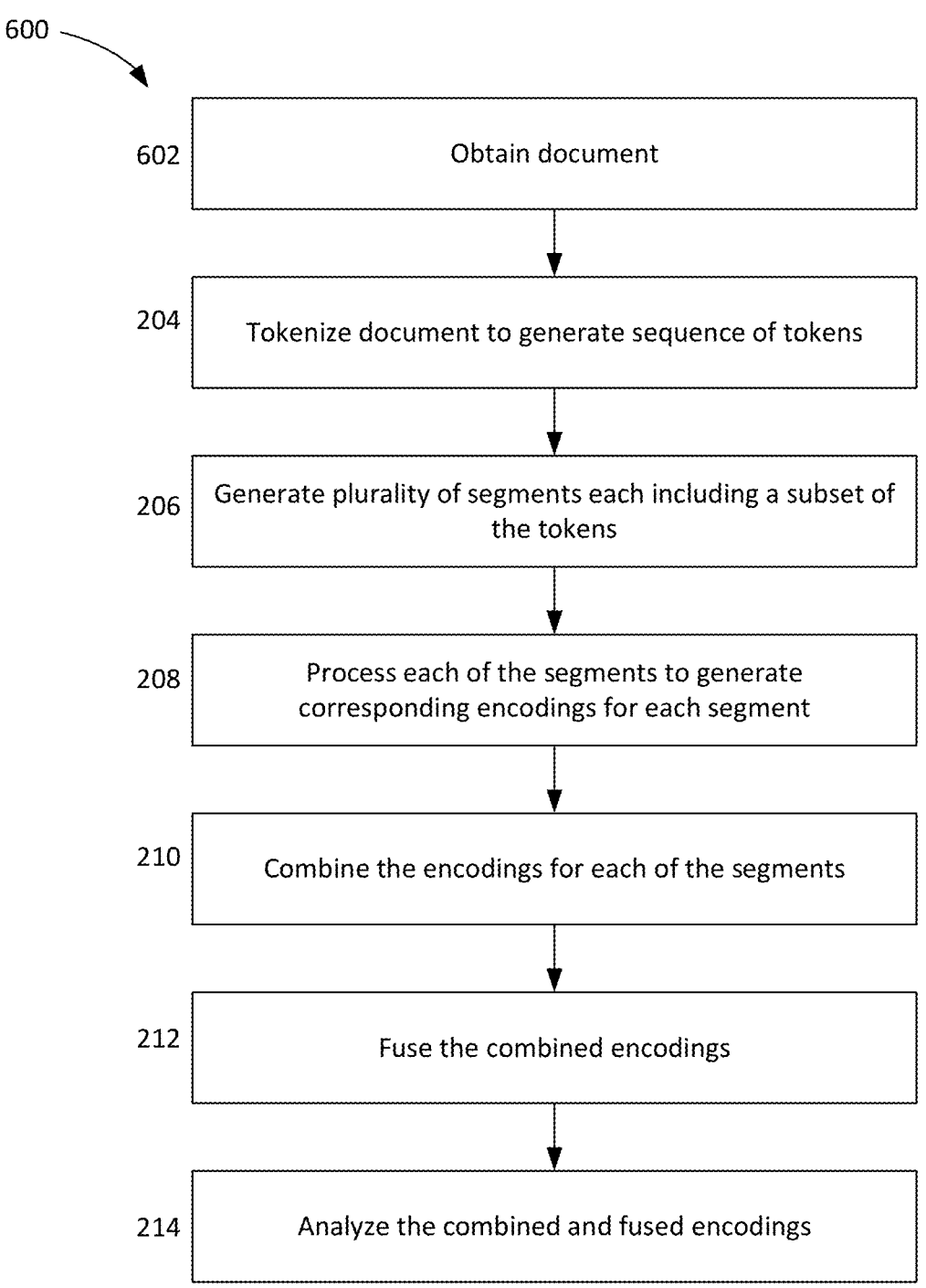
FIG. 6 is an example routine for inferencing using an information retrieval system in accordance with embodiments of the present technology.

With appropriate training (e.g., using the architecture and training approaches described above with respect to FIGS. 2-5), the resulting system can be used for inference tasks on documents outside the training corpus. FIG. 6 is an example routine 600 for inferencing using an information retrieval system. The routine 600 begins in block 602 with obtaining a document. This document may be, for example, a clinical note that is outside the training corpus. In blocks 204-214, the document can be processed similar to the routine 200 described above with respect to FIG. 2. For instance, the document can be tokenized to generate a series of tokens (e.g., at the word level, sub-word level, or otherwise) (block 204). The generated tokens can then be grouped sequentially into segments that each include a subset of the total available tokens (block 206). These segments may be designed to have maximum lengths that are less than a maximum input window for a language model. As such, each of these segments can be processed by a given language model to produce corresponding encodings (block 208). These encodings, which may be word-level encodings, can then be combined (block 210) and fused (block 212) to generate document-level contextual data. Finally, the combined and fused encodings can be analyzed, for instance to perform NER and RE tasks as described previously.

Figure 7:
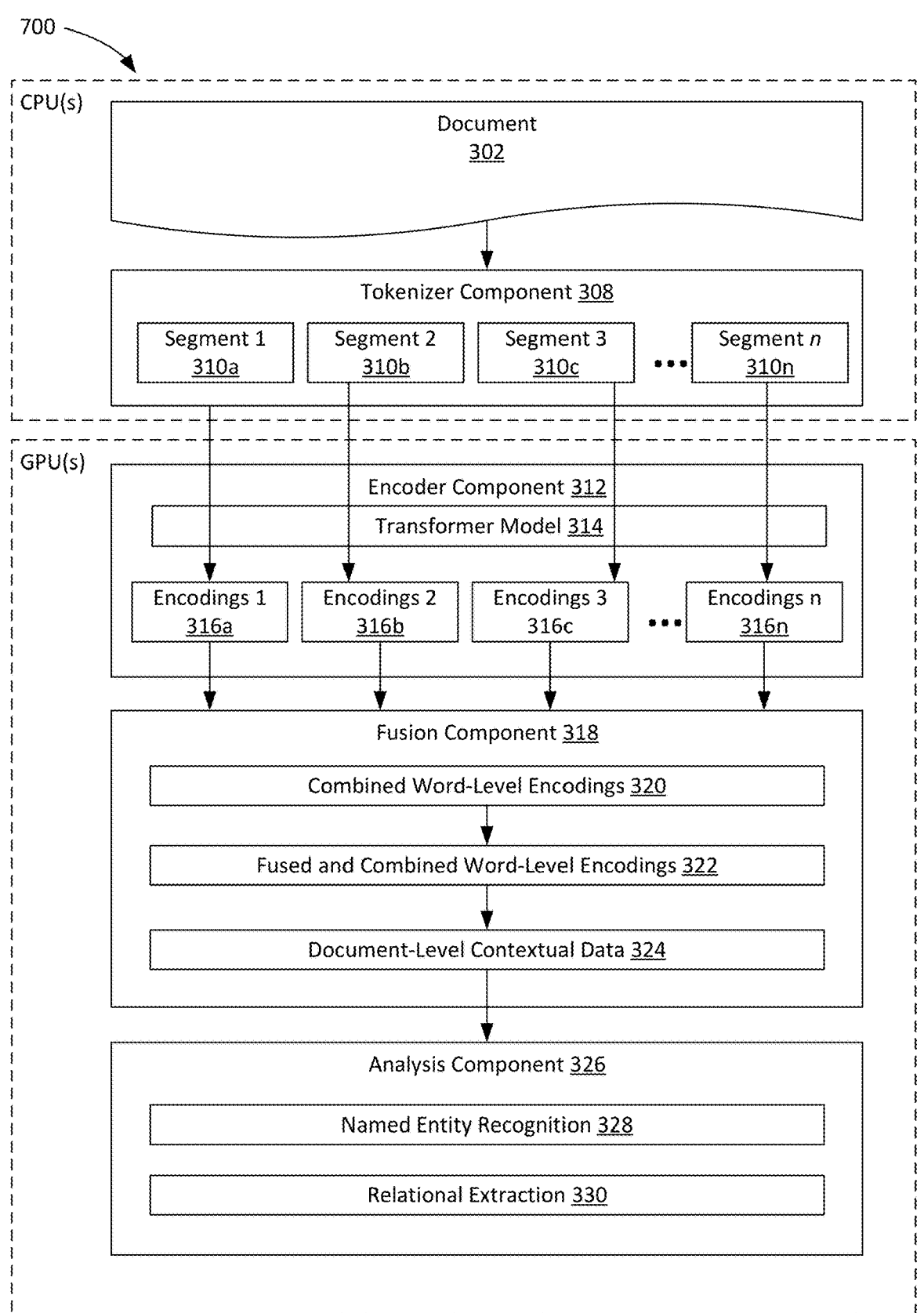
FIG. 7 is a schematic block diagram of inferencing using an information retrieval system in accordance with embodiments of the present technology.

FIG. 7 is a schematic block diagram of inferencing using an information retrieval system 700 in accordance with embodiments of the present technology. The system 700 can include similar components and functionality to the system 300 of FIG. 3 described previously, except the system 700 may omit any training labels or feedback or optimization components configured for training. As illustrated in FIG. 7, a document 302 (e.g., a clinical note outside the training corpus) can be provided to a tokenizer component 308, which both tokenizes the document and groups the tokens sequentially into segments 310. These segments 310 are then provided to an encoding component 312, which includes a transformer model 314 (e.g., a language model such as BERT or other suitable model) that generates corresponding encodings 316 for each segment 310. The encoding may be, or may be processed to be, word-level encodings. These word-level encodings 316 are then combined and fused via fusion component 318 as described previously. The fused and combined word-level encodings 322 can then be provided to the analysis component 326, which can analyze the data, for instance by performing NER and RE tasks (e.g., via named entity recognition prediction component 328 and relational extraction component 330).

As shown in FIG. 7, the initial document processing (e.g., tokenizing and generating segments) can be performed via one or more CPUs, while the remaining processing (e.g., encoding the segments, fusing the encodings, and analyzing the fused encodings) can be performed via one or more GPUs. However, as GPUs generally have access to fewer memory resources than CPUs, this approach can be inefficient for performing inference tasks on very large documents. Additionally, although large documents can be divided into samples for training purposes (e.g., as shown in FIG. 5), this approach may be unsuitable for inference, as doing so may prevent the model from predicting relations where the head and tail entities are in different samples of the same document.

An alternative approach, referred to herein as "hybrid inferencing," can enable inference on long documents under the constraint of CPU memory, instead of GPU memory. Specifically, the intensive attention computation of language models is performed by GPU(s) while the remaining operations (such as fusing encodings via a Bi-LSTM and performing RE and NER predictions via multi-layer perceptrons) are performed on the CPU.

Figure 8:
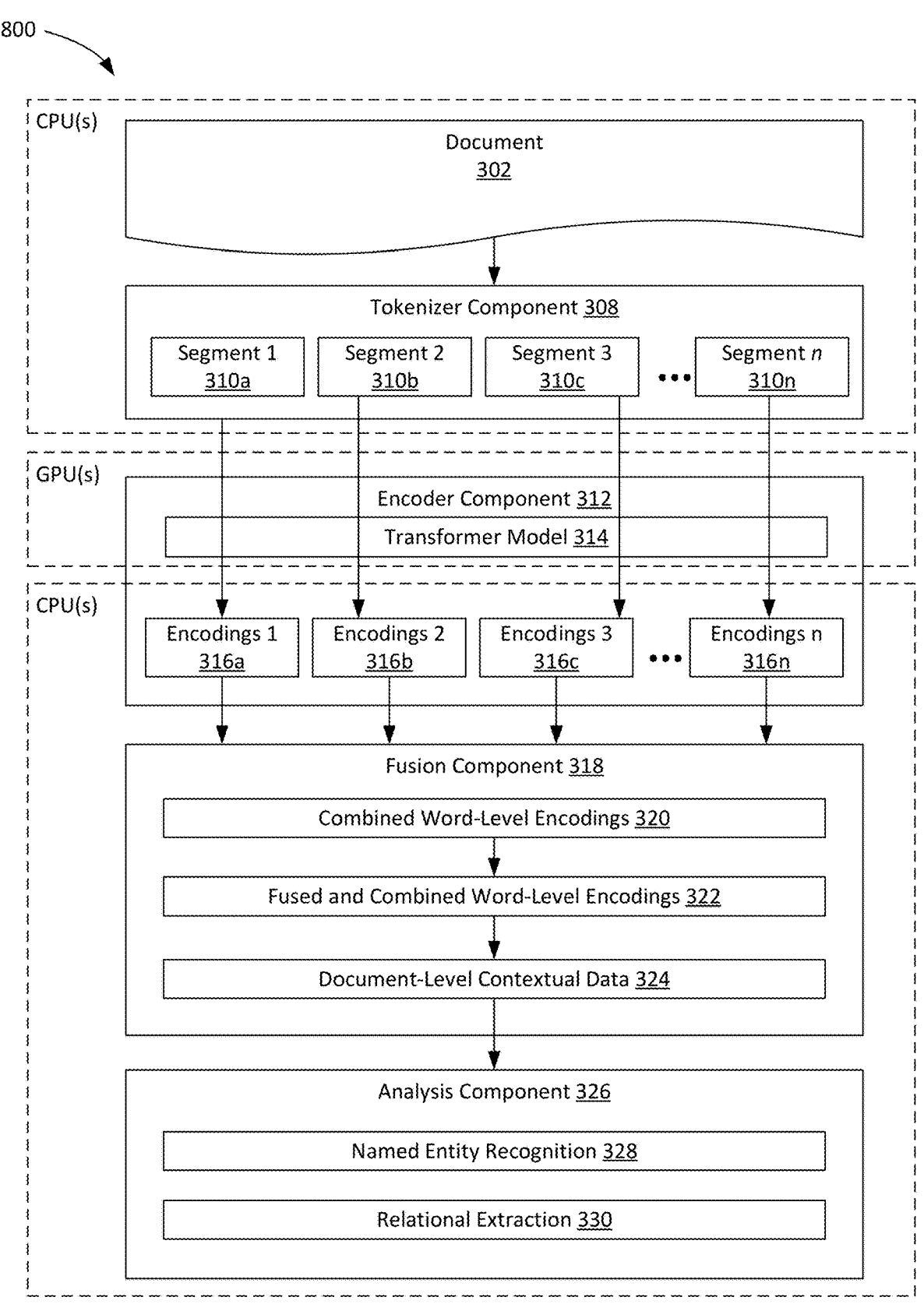
FIG. 8 is a schematic block diagram of a hybrid-inferencing approach using an information retrieval system in accordance with embodiments of the present technology.

An example of this hybrid inferencing architecture is illustrated in FIG. 8, in which tokenizing a document via tokenizer component 308 and grouping the resulting tokens into segments 310 is performed via a first one or more CPUs. Next, using one or more GPUs, the segments are processed via a transformer model 314 to generate corresponding encodings 316. At this stage, instead of keeping all segment encodings on the GPU, they are transferred to the CPU memory as they are generated. Note that, unlike training, which requires keeping intermediate language model features for back-propagation, this approach can recycle GPU memory after encoding each segment during inference. Once all segments have been processed, the segment encodings are combined and fused for analysis (e.g., entity and relation prediction). This approach allows for long document inference even when the size of a document exceeds the GPU memory limit.

III. EXAMPLES

The following examples are included to further describe some aspects of the present technology, and should not be used to limit the scope of the technology.

Example 1. A method comprising: obtaining a document comprising one or more patient health records; tokenizing the document to generate a sequence of tokens each corresponding to a word or sub-word within the document; generating a plurality of segments each containing a token sequence comprising a sub-set of the tokens; processing, via a transformer model, each of the plurality of segments to generate a corresponding word-level encoding for each segment; combining the word-level encodings for each of the plurality of segments; and fusing the combined word-level encodings to obtain document-level contextual data; and analyzing the combined and fused word-level encodings.

Example 2. The method of any one of the preceding Examples, wherein each token corresponds to a word or sub-word within the document.

Example 3. The method of any one of the preceding Examples, wherein analyzing the combined and fused word-level encodings comprises named entity recognition and relation extraction.

Example 4. The method of any one of the preceding Examples, wherein the transformer model has a maximum input window, and wherein each of the plurality of segments is smaller than the maximum input window.

Example 5. The method of any one of the preceding Examples, further comprising first generating sub-word-level encodings, and then generating the word-level encodings based on the sub-word-level encodings.

Example 6. The method of any one of the preceding Examples, wherein the transformer model comprises a bidirectional encoder representations from transformers (BERT) model.

Example 7. The method of any one of the preceding Examples, wherein combining the word-level encodings comprises concatenating the word-level encodings, and wherein fusing the combined word-level encodings comprises applying a bidirectional long short-term memory (bi-LSTM) model to the concatenated word-level encodings.

Example 8. The method of any one of the preceding Examples, wherein each of the tokens is included in one and only one of the segments.

Example 9. The method of any one of the preceding Examples, wherein analyzing the combined and fused word-level encodings comprises using a multi-layer perceptron.

Example 10. The method of any one of the preceding Examples, wherein tokenizing the document and generating the plurality is segments is performed utilizing one or more central processing units (CPUs).

Example 11. The method of any one of the preceding Examples, wherein the processing, via the transformer, each of the plurality of segments to generate the corresponding word-level encoding is performed utilizing one or more graphics processing units (GPUs).

Example 12. The method of any one of the preceding Examples, wherein the combining, fusing, and analyzing are each performed utilizing one or more central processing units (CPUs).

Example 13. The method of any one of the preceding Examples, wherein at least a portion of the processing is performed via one or more graphics processing units (GPUs), and wherein the combining, fusing, and analyzing is performed via one or more central processing units (CPUs).

Example 14. A method comprising: obtaining training data comprising (1) a document including one or more patient health records, (2) a plurality of predetermined named entities associated with the document, and (3) a plurality of predetermined relationships between named entities; tokenizing, via a tokenizer component, the document to generate a sequence of tokens each corresponding to a word or sub-word within the document; generating, via the tokenizer component, a plurality of segments each containing a token sequence comprising a sub-set of the tokens; processing, via an encoding component comprising a transformer model, each of the plurality of segments to generate a corresponding word-level encoding for each segment; combining, via a fusing component, the word-level encodings for each of the plurality of segments; and fusing, via the fusing component, the combined word-level encodings to obtain document-level contextual data; analyzing, via an analysis component, the combined and fused word-level encodings to generate one or more named entity recognition (NER) predictions and one or more relation extraction (RE) predictions; comparing, via a feedback component, the NER predictions with the predetermined named entities and comparing the RE predictions with the predetermined relationships between named entities; based on the comparison, updating weights of one or more of the tokenizer component, the encoding component, or the analysis component.

Example 15. The method of any one of the preceding Examples, wherein comparing, via the feedback component, the NER prediction with the predetermined named entities comprises determining a cross entropy loss.

Example 16. The method of any one of the preceding Examples, wherein comparing, via the feedback component, the RE predictions with the predetermined relationships between named entities comprises determining an adaptive margin loss.

Example 17. The method of any one of the preceding Examples, wherein the tokenizing is performed via one or more central processing units (CPUs).

Example 18. The method of any one of the preceding Examples, wherein the processing, combining, fusing, and analyzing is performed via one or more graphics processing units (GPUs).

Example 19. The method of any one of the preceding Examples, wherein at least a portion of the processing is performed via one or more graphics processing units (GPUs), and wherein the combining, fusing, and analyzing is performed via one or more central processing units (CPUs).

Example 20. The method of any one of the preceding Examples, further comprising obtaining training data comprising (1) a document including one or more patient health records, (2) a plurality of predetermined named entities associated with the document, and (3) a plurality of predetermined relationships between named entities.

Example 21. The method of any one of the preceding Examples, wherein the document comprises one sample among a plurality of samples divided from a parent document, the method further comprising: for each of the plurality of samples, separately performing the tokenizing, generating, processing, combining, fusing, comparing, and updating steps independently for each of the plurality of samples.

Example 22. The method of any one of the preceding Examples, wherein separately performing the tokenizing, generating, processing, combining, fusing, comparing, and updating for each of the plurality of samples comprises utilizing a plurality of graphics processing units (GPUs), wherein the samples are divided among the plurality of GPUs.

Example 23. One or more computer-readable media storing instructions that, when executed by one or more processors of a computing system, cause the computing system to perform operations comprising the method of any one of the preceding Examples.

Example 24. A computing system comprising: one or more processors; and data storage having instructions stored thereon that, when executed by the one or more processors, cause the computing system to perform operations comprising the method of any one of the preceding Examples.

Example 25. A computing system comprising: a tokenizer component configured to tokenize a document to generate a sequence of tokens each corresponding to a word or sub-word within the document, and to generate a plurality of segments each containing a token sequence comprising a sub-set of the tokens; an encoder component comprising a transformer model, the encoding component configured to generate a corresponding word-level encoding for each of the plurality of segments; a fusion component configured to combine the word-level encodings for each of the plurality of segments and fuse the combined word-level encodings to obtain document-level contextual data; an analysis component configured to analyze the combined and fused word-level encodings to generate one or more predictions.

IV. CONCLUSION

Although many of the embodiments are described above with respect to systems, devices, and methods for indexing and searching patient data, the technology is applicable to other applications and/or other approaches, such as indexing and/or searching other types of data (e.g., financial records, educational records, political information, location data, and/or other personal information). Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-8.

The various processes described herein can be partially or fully implemented using program code including instructions executable by one or more processors of a computing system for implementing specific logical functions or steps in the process. The program code can be stored on any type of computer-readable medium, such as a storage device including a disk or hard drive. Computer-readable media containing code, or portions of code, can include any appropriate media known in the art, such as non-transitory computer-readable storage media. Computer-readable media can include volatile and non-volatile, removable and non-removable media implemented in any method or technology for storage and/or transmission of information, including, but not limited to, random-access memory (RAM), read-only memory (ROM), electrically erasable programmable read-only memory (EEPROM), flash memory, or other memory technology; compact disc read-only memory (CD-ROM), digital video disc (DVD), or other optical storage;

magnetic cassettes, magnetic tape, magnetic disk storage, or other magnetic storage devices; solid state drives (SSD) or other solid state storage devices; or any other medium which can be used to store the desired information and which can be accessed by a system device.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:

1. A method, performed by a computing system having one or more processors and one or more memories, the method comprising:

obtaining a document comprising one or more patient health records;

tokenizing the document to generate a sequence of tokens each corresponding to a word or sub-word within the document;

generating a plurality of segments each containing a token sequence comprising a sub-set of the tokens;

processing, via a transformer model, each of the plurality of segments to generate a corresponding word-level encoding for each segment;

combining the word-level encodings for each of the plurality of segments; and fusing the combined word-level encodings to obtain document-level contextual data; and analyzing the combined and fused word-level encodings.

2. The method of claim 1, wherein each token corresponds to a word or sub-word within the document.

3. The method of claim 1, wherein analyzing the combined and fused word-level encodings comprises named entity recognition and relation extraction.

4. The method of claim 1, wherein the transformer model has a maximum input window, and wherein each of the plurality of segments is smaller than the maximum input window.

5. The method of claim 1, further comprising first generating sub-word-level encodings, and then generating the word-level encodings based on the sub-word-level encodings.

6. The method of claim 1, wherein the transformer model comprises a bidirectional encoder representations from transformers (BERT) model.

7. The method of claim 1, wherein combining the word-level encodings comprises concatenating the word-level encodings, and wherein fusing the combined word-level encodings comprises applying a bidirectional long short-term memory (bi-LSTM) model to the concatenated word-level encodings.

8. The method of claim 1, wherein each of the tokens is included in one and only one of the segments.

9. The method of claim 1, wherein analyzing the combined and fused word-level encodings comprises using a multi-layer perceptron.

10. The method of claim 1, wherein tokenizing the document and generating the plurality of segments is performed utilizing one or more central processing units (CPUs).

11. The method of claim 1, wherein the processing, via the transformer, each of the plurality of segments to generate the corresponding word-level encoding is performed utilizing one or more graphics processing units (GPUs).

12. The method of claim 1, wherein the combining, fusing, and analyzing are each performed utilizing one or more central processing units (CPUs).

13. The method of claim 1, wherein at least a portion of the processing is performed via one or more graphics processing units (GPUs), and wherein the combining, fusing, and analyzing is performed via one or more central processing units (CPUs).

14. One or more computer-readable media storing instructions that, when executed by one or more processors of a computing system, cause the computing system to perform operations comprising:

obtaining training data comprising (1) a document including one or more patient health records, (2) a plurality of predetermined named entities associated with the document, and (3) a plurality of predetermined relationships between named entities;

tokenizing, via a tokenizer component, the document to generate a sequence of tokens each corresponding to a word or sub-word within the document;

generating, via the tokenizer component, a plurality of segments each containing a token sequence comprising a sub-set of the tokens;

processing, via an encoding component comprising a transformer model, each of the plurality of segments to generate a corresponding word-level encoding for each segment;

combining, via a fusing component, the word-level encodings for each of the plurality of segments;

fusing, via the fusing component, the combined word-level encodings to obtain document-level contextual data;

analyzing, via an analysis component, the combined and fused word-level encodings to generate one or more named entity recognition (NER) predictions and one or more relation extraction (RE) predictions;

comparing, via a feedback component, the one or more NER predictions with the predetermined named entities and comparing the RE predictions with the predetermined relationships between named entities; and based on the comparison, updating weights of one or more of the tokenizer component, the encoding component, or the analysis component.

15. The one or more computer-readable media of claim 14, wherein comparing, via the feedback component, the one or more NER predictions with the predetermined named entities comprises determining a cross entropy loss.

16. The one or more computer-readable media of claim 14, wherein comparing, via the feedback component, the RE predictions with the predetermined relationships between named entities comprises determining an adaptive margin loss.

17. The one or more computer-readable media of claim 14, wherein the processing, combining, fusing, and analyzing is performed via one or more graphics processing units (GPUs).

18. The one or more computer-readable media of claim 14, wherein the document comprises one sample among a plurality of samples divided from a parent document, the operations further comprising:

for each of the plurality of samples, separately performing the tokenizing, generating, processing, combining, fusing, comparing, and updating steps independently for each of the plurality of samples.

19. The one or more computer-readable media of claim 18, wherein separately performing the tokenizing, generating, processing, combining, fusing, comparing, and updating for each of the plurality of samples comprises utilizing a plurality of graphics processing units (GPUs), wherein the samples are divided among the plurality of GPUs.

20. A computing system comprising:

one or more processors;

one or more memories;

a tokenizer component configured to tokenize a document to generate a sequence of tokens each corresponding to a word or sub-word within the document, and to generate a plurality of segments each containing a token sequence comprising a sub-set of the tokens;

an encoder component comprising a transformer model, the encoding component configured to generate a corresponding word-level encoding for each of the plurality of segments;

a fusion component configured to combine the word-level encodings for each of the plurality of segments and fuse the combined word-level encodings to obtain document-level contextual data; and an analysis component configured to analyze the combined and fused word-level encodings to generate one or more predictions, wherein each component comprises computer-executable instructions stored in the one or more memories for execution by the computing system.

* * * * *